United States Patent [19]

Norman

[11] Patent Number: 4,716,609
[45] Date of Patent: Jan. 5, 1988

[54] DOMICILE FOR LEAF CUTTER BEES

[76] Inventor: Frederick A. Norman, 21 Greensview Road, Banksia Park, S.A., Australia

[21] Appl. No.: 832,784

[22] Filed: Feb. 26, 1986

[51] Int. Cl.$^4$ .............................................. A01K 47/00
[52] U.S. Cl. .................................................... 6/1
[58] Field of Search ........................................ 6/1, 2 R

[56] References Cited

U.S. PATENT DOCUMENTS

| | | | |
|---|---|---|---|
| 2,169,858 | 8/1939 | Turchenko | 6/1 |
| 2,593,296 | 4/1952 | Green | 6/1 X |
| 4,402,099 | 9/1983 | Platt, Jr. | 6/1 |
| 4,491,994 | 1/1985 | Youssef | 6/1 |

FOREIGN PATENT DOCUMENTS 784846 12/1980 U.S.S.R. ..................................... 6/1

Primary Examiner—Robert P. Swiatek
Attorney, Agent, or Firm—Millen & White

[57] ABSTRACT

A domicile for leaf cutter bees includes front, end and rear panels, a base and top panel and a lid of weather resistant material. The domicile is supported on legs which are fitted to the end panels and to each of which there is fitted an angle bracket carrying an upstanding locating pin. The base is inserted between the end panels and located by holes engaging over the locating pins. The tops of the end panels are provided with a bracket carrying locating pins over which the top panel is located. The top panel has cross angle members attached by bolts or pin hangers. The lid is fitted over the top panel and located by the locating pins. Guy wires are fitted to the locating pins to stabilize the unit. The nest holder is suspended from the top panel by a hanger, each nest being a plurality of blind tunnels.

17 Claims, 7 Drawing Figures

DOMICILE FOR LEAF CUTTER BEES

BACKGROUND OF THE INVENTION

This invention relates to the husbandry and management techniques of leaf cutter bees (Megachile Rotundata) and to their protection during pollination and active life cycle and procreation of their kind during the period from incubation until cessation of adult life.

Leaf cutter bees are ideally suited for the pollination of lucerne and some form of domicile and protection is required for these bees during their life cycle, particularly from the natural elements such as damp or wet weather, extremes of heat, protection from predators and pests including termites, rodents and like creatures for these been themselves have no defence against any enemies.

It is an object of this invention to provide a portable domicile to house the nests required for the breeding of the young, it being necessary to provide a transportable or portable domicile which will protect against the natural elements and enemies noted above.

In one form of the invention the domicile can be provided by a collapsable framework, the framework housing the next holder and providing protection against its predators.

SUMMARY OF THE INVENTION

This invention relates to a domicile for leaf cutter bees, said domicile comprising a structure providing access to bees but preventing entry of pests and animals, a nest holder supported by hangers from an upper portion of the structure whereby free circulation of air is available over the nest holder while protecting the nest holder from the environment.

BRIEF DESCRIPTION OF DRAWINGS

One form of domicile is described in relation to the accompanying drawings, in which.

DETAILED DISCUSSION

Figure 1:
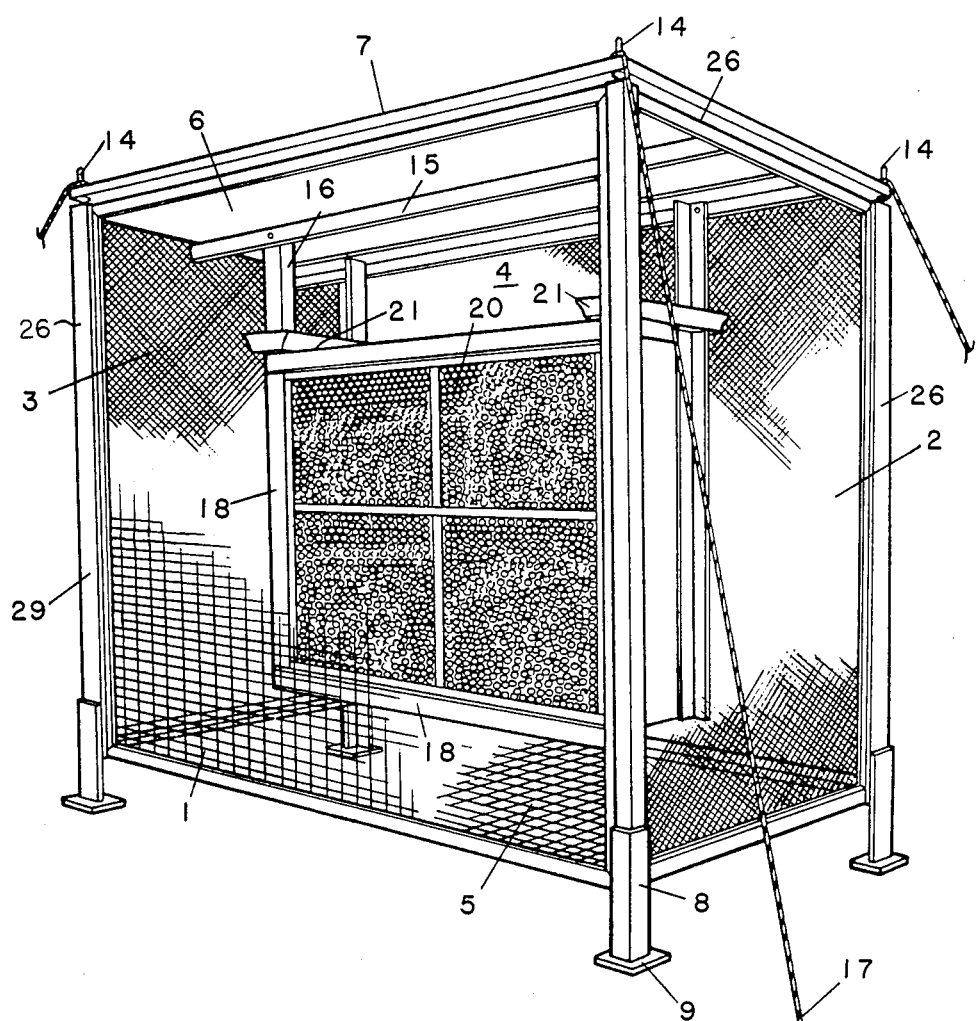
FIG. 1 is a perspective view of the domicile.

The domicile includes a front panel 1, end panels 2 and 3, rear panel 4, base 5, top panel 6 and lid 7. The domicile is supported on legs 8, each having a base 9. The legs can be fitted to the end panels 2 and 3, either by the panels fitting into the angle sections 10 of the legs to be bolted thereto, or to be permanently fixed thereto by bolting, rivetting or welding.

Figure 2:
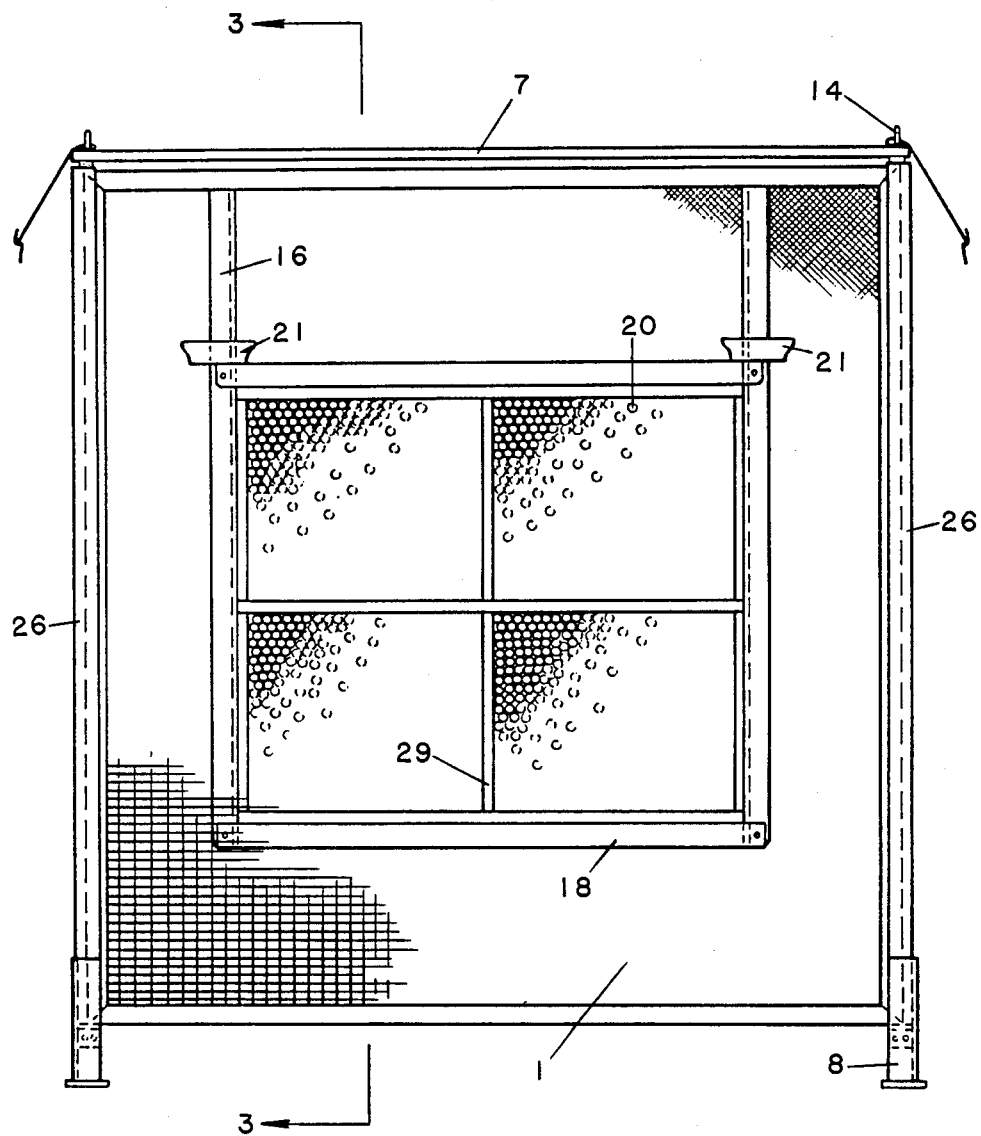
FIG. 2 is a front sectional view.
Figure 3:
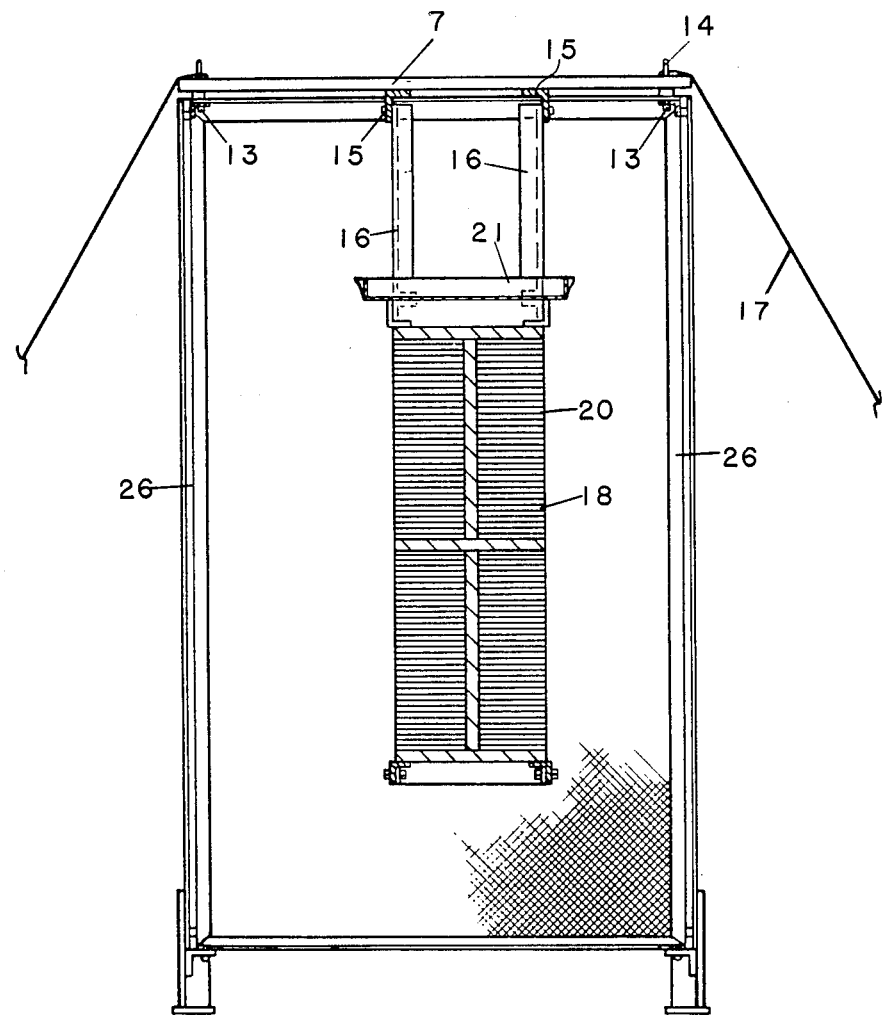
FIG. 3 is an end sectional view.
Figure 4:
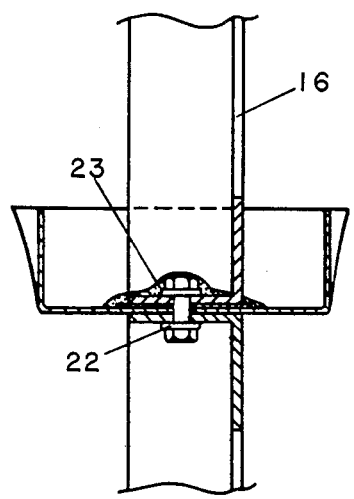
FIG. 4 is a view of an insect trap.
Figure 5:
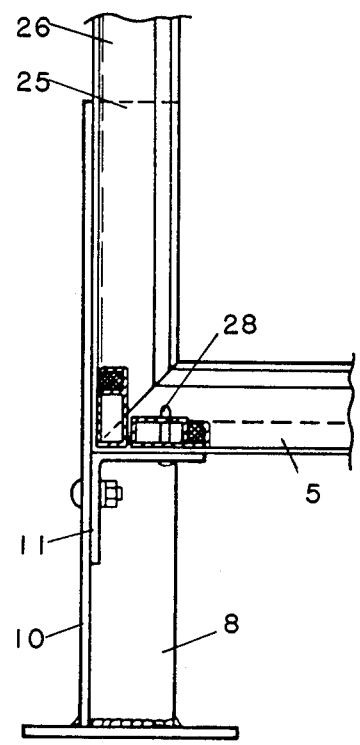
FIG. 5 is a front view of a corner post in cross-section.
Figure 6:
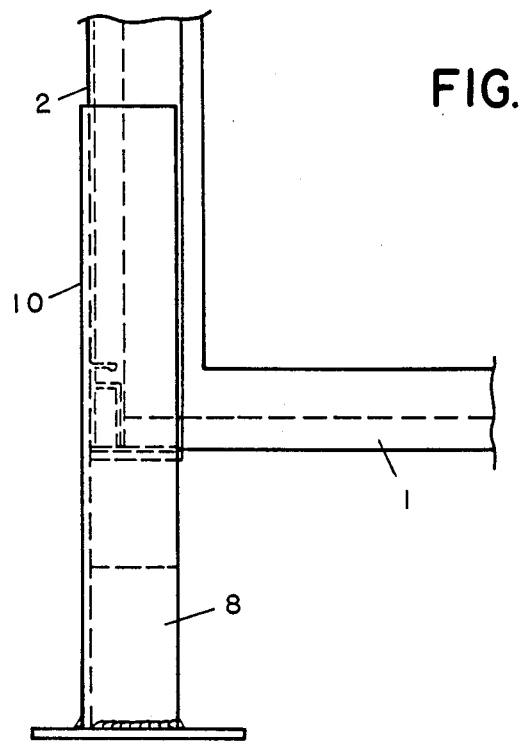
FIG. 6 is a view of the corner post.
Figure 7:
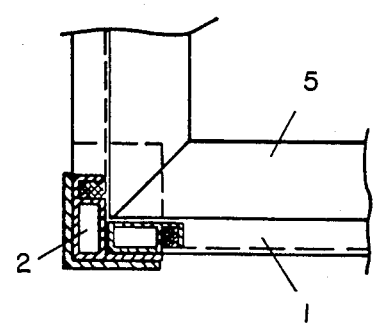
FIG. 7 is a cross-section in plan of the corner post.

To each of the legs there is fitted by rivetting, bolting or welding an angle bracket 11 carrying an upstanding locating pin 28 (see FIG. 2). The base 5 is inserted between the end panels 2 and 3 and located by holes in the base engaged by the locating pins 28 (see FIG. 5). The end panels 2 and 3 at their top are provided with a bracket 13 (see FIG. 3) carrying locating pins 14 over which the lid 7 is located. The panels support cross angle members 15 to which are attached by bolts or pins four hangers 16. The lid 7 is fitted over the top edges of the side panels, the lid being of weather resistant material and being located by the pins 14. Guy wires 17 are fitted to the locating pins 14 to stabilise the unit.

The next holder 18 is suspended by the hanger 16, each next being a plurality of blind tunnels 20 constructed or formed from any suitable materials such as bored or grooved boards placed in blocks or groups within the holder framework.

Cost of nests and space required for same can be reduced by providing banks of blind paper straw tunnels, for example, drinking straws which are offered complete protection within domiciles during course of breeding cycle of bees concerned.

The nests of any type can be readily removed from domicile in field for storage in cool rooms for diapause stage prior to dismantling of domicile, cells can then be harvested from tunnels by various means, dependent upon techniques of husbandry being practised. The frame for the nest holder 18 can be an aluminium angle frame bolted together with polystyrene foam dividing strips 29.

On each of the hangers 16 there is fitted an insect trap 21 formed of sheet metal without seams, clamped between two portions of the hanger 16 by a bolt with neoprene and steel washers 22 and an oil resistant sealer 23. An oil or like substance is placed in the trap 21 to prevent insects crawling down the hangers 16.

The domicile can be dismantled and assembled as desired. The front and rear panels are inserted by sliding into a slot behind side flanges 25 in vertical supports 26 at the top in the upper frame, and then lowered to locate over pegs or pins 28 at the bottom (see FIG. 5). Similarly the bottom pnel is located over the pegs and also the top panel and lid similarly located. Hence the domicile can be moved and located to the desired position.

For a further alternative the domicile can be provided with an insulated top to which are hinged the end walls carrying supporting feet.

The hinges are such that one side wall can be folded against the top panel and then the second side wall folded to be in parallel relationship to the first folded panel.

When the side walls are in their spread condition, a base frame is inserted between the side walls, this being either clipped or releasably retained to the side walls in any desired manner.

Removable screens for the front and rear of the domicile can then be positioned to enclose the space within the domicile.

In both embodiments the nest holder is provided within the domicile this being such that air space is provided completely around the nest holder, and thus the nest holder can be suspended from the ceiling, oil traps or the like being provided on the suspension means to prevent insects and the like from crawling down the suspension means.

The nest holder can hold a plurality of nests, for example four, each of the nests comprising blind tunnels, and the nest holder could thus provide a basis of twenty thousand blind tunnels to accommodate five thousand to six thousand bees which are considered a suitable number to pollinate one area of crop and with correct placement, the bees can be kept within this area, or as shown 8 nests can accommodate forty thousand tunnels for ten to twelve thousand bees.

Thus it will be seen that the domiciles are constructed of six panels which are each readily and rapidly assembled and dismantled by one person, the two side panels and rear panel being of a metal frame faced with woven wire or expanded metal to prevent flying insects having access to the interior, but permitting air to flow through the sections while still protecting the nest holder from the elements.

The front and base panels again are of metal frames faced with wire screens to restrict entry of birds.

Depending upon the climate, one or more of the end and rear panels may be formed of insulating material. For example in colder climates the insulated panels will help to maintain the temperature of the domicile at a warmer temperature by trapping the heat therein. Tus one or more panels can be of heat absorbing material while in hot climates one or more panels may of heat reflective material.

The domicile is assembled in a preferred area, and restrained by guide wires fixed to each top corner and thence to steel stakes driven into the ground.

The incubated bees are placed from incubation in a suitable release container inside the domicile resting on an inner side of the base from whence te bees proceed to select tunnels in the nests which have been previously placed in position.

The advantages of the preferred domicile against any other known unit of providing artificial nesting and dormitary accommodation for the leaf cutter bees, are than concentration of the bees and the crop can be readily controlled by those numbers necessary to pollinate a pasture area, with the bees being kept within the desired area.

The harvesting of the cells from activity of bee during its life cycle can be readily and easily monitored along with the pollination effect on the surrounding area from the domicile.

Thus it will be seen that the domiciles are constructed of durable construction, are readily dismantled for storage during diapause stage of the bee, and then re-erected for the following pollination season and thus permit the owner of the bees to give maximum possible protection to his livestock as well as harvesting the total progeny for future needs and increasing bee numbers.

While it will be seen that one form of the invention has been described in some detail it is to be realised that variations can be made, for example in supporting the cell holder in such a way that it is virtually isolated from the surrounding framework.

Also variations can be made in the particular manner in which the unit folds for disassembly and these variations are intended to be considered within the scope of the present invention.

What is claimed is:

1. A domicile for leaf cutter bees, the domicile comprising:
    a supporting frame having a plurality of struts defining an enclosure, the enclosure having a top, a base and sides;
    mesh means connected to the struts for defining porous surfaces for the enclosure through which surfaces the leaf cutter bees can enter the enclosure,
    a solid panel means having an impermeable surface disposed at least over the top of the enclosure to shield the enclosure from rain and sun; the panel means cooperating with the mesh means to completely surround the enclosure;
    a nest holder within the enclosure for supporting a nest for the bees, and
    hanger means for suspending the nest holder from the top of the enclosure in spaced relation to the top, base and sides of the enclosure.

2. A domicile as defined in claim 1 wherein the frame is a collapsible structure the sides of which include front and rear panels joined by end panels, the end panels having supporting legs, with said base being supported on brackets having locating pins to support and locate the base.

3. A domicile as defined in claim 2 wherein the front and rear panels are positioned by engaging behind side flanges, and are supported on the base by pins upstanding from the base.

4. A domicile as defined in claim 3 wherein each hanger means incorporates an insect trap to prevent insects crawling down the hanger means.

5. A domicile as defined in claim 3 wherein the domicile is stabilized by guy ropes or wires from top corners thereof.

6. A domicile as defined in claim 3 wherein the solid panels means is a lid; wherein each hanger means incorporates an insect trap to prevent insects crawling down the hanger means; wherein the structure us stabilized by guy ropes and wires from top corners thereof; and wherein the next holder comprises a plurality of blind tubes for accomodating cells of the hive.

7. A domicile as defined in claim 2 wherein the top panel is a lid.

8. A domicile as defined in claim 7 wherein each hanger means incorporating an insect trap to prevent insects crawling down the hangers.

9. A domicile as defined in claim 7 wherein the domicile is stabilized by guy ropes or wires from top corners thereof.

10. A domicile as defined in claim 2 wherein the frame is stabilised by guy ropes or wires from the top corners.

11. A domicile as defined in claim 2 wherein one or more of the panels are of insulating material or of heat reflective material.

12. A domicile as defined in claim 1 wherein the nest holder comprises a plurality of compartments, each compartment containing a plurality of blind tubes for the cells.

13. A domicile as defined in claim 1 wherein each hanger means incorporates an insect trap to prevent insects crawling down the hanger means.

14. A domicile for leaf cutter bees, said domicile comprising a structure providing access to bees, but preventing entry of pests and animals, the structure being collapsible and including front and rear panels joined by end panels, a base and a roof, the end panels having supporting legs with the base being supported on brackets having locating pins to support and locate the base; hangers depending from the roof, each hanger incorporating an insect trap for preventing insects from crawling down the hangers, and a nest holder supported by the hangers in spaced relation with the roof whereby free circulation of air is available over the nest holder while protecting the nest holder from the environment.

15. The domicile of claim 14 wherein one or more of the panels are of mesh material.

16. The domicile of claim 14 wherein one or more of the panels are of insulating material or heat reflective material.

17. The domicile of claim 14 wherein the nest holder comprises a plurality of compartments, each compartment containing a plurality of blind tubes for accommodating cells of a hive.

* * * * *